United States Patent
Moskowitz et al.

(10) Patent No.: US 8,740,833 B2
(45) Date of Patent: *Jun. 3, 2014

(54) ANTI-THROMBOGENIC VENOUS SHUNT METHOD

(75) Inventors: Ari Moskowitz, Santa Barbara, CA (US); William J. Bertrand, Ventura, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/184,981

(22) Filed: Jul. 18, 2011

(65) Prior Publication Data

US 2011/0275975 A1    Nov. 10, 2011

Related U.S. Application Data

(62) Division of application No. 11/119,339, filed on Apr. 29, 2005, now Pat. No. 8,002,730.

(51) Int. Cl.

| | |
|---|---|
| *A61M 1/00* | (2006.01) |
| *A61L 33/00* | (2006.01) |
| *A61M 27/00* | (2006.01) |
| *A61M 39/02* | (2006.01) |
| *A61M 25/00* | (2006.01) |
| *A61M 39/24* | (2006.01) |

(52) U.S. Cl.
CPC ............ *A61M 27/006* (2013.01); *A61M 27/002* (2013.01); *A61M 39/0208* (2013.01); *A61M 2205/3331* (2013.01); *A61M 2025/0025* (2013.01); *A61M 2039/242* (2013.01); *A61M 2039/2493* (2013.01); *A61M 2210/0687* (2013.01); *A61M 2210/0693* (2013.01); *A61M 2202/0464* (2013.01)
USPC ...... 604/8; 604/9; 604/10; 604/264; 604/266; 424/422; 424/423

(58) Field of Classification Search
CPC .................. A61M 27/006; A61M 2205/3331; A61M 25/00; A61M 27/002; A61M 2025/0025; A61M 2027/002; A61M 2039/242; A61M 2039/2426; A61M 2039/2433; A61M 2039/2473; A61M 2039/2493; A61M 2210/0687; A61M 2210/0693; A61M 2202/0464
USPC .......... 604/8, 9, 10, 264, 266; 623/1.42, 1.43, 623/1.45, 1.46; 424/422, 423, 424, 425
See application file for complete search history.

(56) References Cited

U.S. PATENT DOCUMENTS

| | | | |
|---|---|---|---|
| 3,595,240 | A | 7/1971 | Mishler |
| 3,598,127 | A | 8/1971 | Wepsic |

(Continued)

FOREIGN PATENT DOCUMENTS

| | | |
|---|---|---|
| EP | 1 649 880 A | 4/2006 |
| WO | WO 2006/015091 A | 2/2006 |
| WO | WO 2004/073768 A | 9/2006 |

OTHER PUBLICATIONS

Damen, Eric W.P. et al., "Paclitaxel esters of malic acid as prodrugs with improved water solubility," Bioorganic & Medicinal Chemistry, vol. 8, Issue 2, Feb. 2000, pp. 427-432.

(Continued)

*Primary Examiner* — Adam Marcetich
(74) *Attorney, Agent, or Firm* — IPLM Group, P.A.

(57) ABSTRACT

A venous shunt method adapted to shunt cerebral spinal fluid in a patient. A fluid control device having a fluid passage is adapted to be placed allowing cerebral spinal fluid to flow through the fluid passage. A catheter having a lumen, the catheter being in fluid communication with the fluid control device. At least a portion of at least one of the catheter and the fluid control device being subjected to an anti-thrombogenic treatment.

4 Claims, 3 Drawing Sheets

(56) References Cited

U.S. PATENT DOCUMENTS

| Patent No. | | Date | Inventor(s) | Ref |
|---|---|---|---|---|
| 3,683,929 A | | 8/1972 | Holter | |
| 3,827,439 A | * | 8/1974 | Schulte et al. | 604/9 |
| 3,889,687 A | | 6/1975 | Harris | |
| 4,212,308 A | | 7/1980 | Percarpio | |
| 4,364,395 A | | 12/1982 | Redmond et al. | |
| 4,578,057 A | * | 3/1986 | Sussman | 604/9 |
| 4,588,085 A | * | 5/1986 | Sussman | 206/438 |
| 4,605,395 A | | 8/1986 | Rose et al. | |
| 4,610,658 A | * | 9/1986 | Buchwald et al. | 604/9 |
| 4,621,654 A | | 11/1986 | Holter | |
| 4,623,329 A | | 11/1986 | Drobish et al. | |
| 4,675,003 A | | 6/1987 | Hooven | |
| 4,681,559 A | * | 7/1987 | Hooven | 604/9 |
| 4,698,058 A | | 10/1987 | Greenfeld et al. | |
| 4,722,906 A | | 2/1988 | Guire | |
| 4,741,730 A | * | 5/1988 | Dormandy et al. | 604/8 |
| 4,781,673 A | | 11/1988 | Watanabe | |
| 4,787,886 A | | 11/1988 | Cosman | |
| 4,816,016 A | | 3/1989 | Schulte et al. | |
| 4,861,331 A | | 8/1989 | East et al. | |
| 4,867,740 A | * | 9/1989 | East | 604/9 |
| 4,883,456 A | | 11/1989 | Holter | |
| 4,916,193 A | | 4/1990 | Tang et al. | |
| 4,950,232 A | * | 8/1990 | Ruzicka et al. | 604/43 |
| 4,973,493 A | | 11/1990 | Guire | |
| 4,979,959 A | | 12/1990 | Guire | |
| 4,994,071 A | | 2/1991 | MacGregor | |
| 5,000,731 A | * | 3/1991 | Wong et al. | 604/8 |
| 5,002,582 A | | 3/1991 | Guire et al. | |
| 5,112,303 A | | 5/1992 | Pudenz et al. | |
| 5,217,492 A | | 6/1993 | Guire et al. | |
| 5,221,698 A | | 6/1993 | Amidon et al. | |
| 5,258,041 A | | 11/1993 | Guire et al. | |
| 5,263,992 A | * | 11/1993 | Guire | 623/66.1 |
| 5,300,059 A | | 4/1994 | Rubinstein et al. | |
| 5,304,121 A | | 4/1994 | Sahatjian | |
| 5,336,166 A | * | 8/1994 | Sierra | 604/9 |
| 5,405,316 A | * | 4/1995 | Magram | 604/8 |
| 5,464,650 A | | 11/1995 | Berg et al. | |
| 5,500,013 A | | 3/1996 | Buscemi et al. | |
| 5,512,329 A | | 4/1996 | Guire et al. | |
| 5,562,617 A | | 10/1996 | Finch et al. | |
| 5,660,200 A | | 8/1997 | Paes | |
| 5,674,177 A | | 10/1997 | Hehrlein et al. | |
| 5,683,357 A | | 11/1997 | Magram | |
| 5,697,951 A | | 12/1997 | Harpstead et al. | |
| 5,713,859 A | | 2/1998 | Finch et al. | |
| 5,741,551 A | | 4/1998 | Guire et al. | |
| 5,807,356 A | | 9/1998 | Finch et al. | |
| 5,830,172 A | * | 11/1998 | Leveen et al. | 604/9 |
| 5,858,653 A | | 1/1999 | Duran et al. | |
| 5,873,865 A | | 2/1999 | Horzewski et al. | |
| 5,925,054 A | | 7/1999 | Taylor et al. | |
| 5,942,555 A | | 8/1999 | Swanson et al. | |
| 6,030,358 A | | 2/2000 | Odland | |
| 6,053,901 A | | 4/2000 | Finch et al. | |
| 6,056,717 A | | 5/2000 | Finch et al. | |
| 6,077,698 A | | 6/2000 | Swan et al. | |
| 6,095,997 A | | 8/2000 | French et al. | |
| 6,110,155 A | | 8/2000 | Baudino | |
| 6,121,027 A | | 9/2000 | Clapper et al. | |
| 6,214,022 B1 | | 4/2001 | Taylor et al. | |
| 6,214,901 B1 | | 4/2001 | Chudzik et al. | |
| 6,264,595 B1 | | 7/2001 | Delfino et al. | |
| 6,267,775 B1 | | 7/2001 | Clerc et al. | |
| 6,278,018 B1 | | 8/2001 | Swan | |
| 6,344,035 B1 | | 2/2002 | Chudzik et al. | |
| 6,348,042 B1 | | 2/2002 | Warren, Jr. | |
| 6,603,040 B1 | | 8/2003 | Swan | |
| 6,626,902 B1 | | 9/2003 | Kucharczyk et al. | |
| 6,706,408 B2 | | 3/2004 | Jelle | |
| 6,926,735 B2 | | 8/2005 | Henderson | |
| 7,322,954 B2 | | 1/2008 | Putz | |
| 8,002,730 B2 | | 8/2011 | Moskowitz | |
| 2002/0026138 A1 | | 2/2002 | Cowan et al. | |
| 2003/0039689 A1 | | 2/2003 | Chen et al. | |
| 2003/0045870 A1 | | 3/2003 | Madsen | |
| 2003/0069541 A1 | | 4/2003 | Gillis et al. | |
| 2003/0114791 A1 | * | 6/2003 | Rosenthal et al. | 604/96.01 |
| 2003/0135147 A1 | * | 7/2003 | Rosenberg et al. | 604/8 |
| 2003/0163079 A1 | * | 8/2003 | Burnett | 604/9 |
| 2003/0171738 A1 | * | 9/2003 | Konieczynski et al. | 604/891.1 |
| 2003/0187367 A1 | | 10/2003 | Odland | |
| 2004/0030218 A1 | | 2/2004 | Kocur et al. | |
| 2004/0073157 A1 | | 4/2004 | Knudson et al. | |
| 2004/0082900 A1 | * | 4/2004 | Luttich | 604/9 |
| 2004/0147871 A1 | * | 7/2004 | Burnett | 604/9 |
| 2004/0220510 A1 | | 11/2004 | Koullick et al. | |
| 2004/0236416 A1 | * | 11/2004 | Falotico | 623/1.42 |
| 2005/0033417 A1 | * | 2/2005 | Borges et al. | 623/1.46 |
| 2005/0079199 A1 | | 4/2005 | Heruth et al. | |
| 2005/0100580 A1 | * | 5/2005 | Osborne et al. | 424/424 |
| 2005/0125054 A1 | | 6/2005 | Bhat et al. | |
| 2005/0208092 A1 | | 9/2005 | Falotico et al. | |
| 2006/0004317 A1 | | 1/2006 | Mauge et al. | |
| 2006/0074371 A1 | * | 4/2006 | McCusker et al. | 604/9 |
| 2006/0074388 A1 | | 4/2006 | Dextradeur et al. | |
| 2006/0247569 A1 | | 11/2006 | Bertrand et al. | |
| 2006/0258970 A1 | | 11/2006 | Moskowitz et al. | |
| 2007/0055196 A1 | | 3/2007 | Gormley | |
| 2007/0123973 A1 | | 5/2007 | Roth et al. | |

OTHER PUBLICATIONS

Drug Digest, Drugs & Vitamins, Drug Library, *Urokinase*, 3 pgs., product description, accessed Feb. 15, 2005.

ICU AU Procedural Manual, *Steptokinase*, 4 pgs, accessed Feb. 15, 2005.

Medtronic, Inc., *Cranial Repair*, product description, 4 pgs, accessed Feb. 16, 2005.

Streptase Pharmacology, Pharmacokinetics, Studies, Metabolism, *Clinical Pharmacology*, 3 pgs., product description, accessed Feb. 15, 2005.

Webpage www.netdoctor.co.uk-medicines, *Streptokinase*, 2 pgs, accessed Feb. 15, 2005.

* cited by examiner

ANTI-THROMBOGENIC VENOUS SHUNT METHOD

RELATED APPLICATIONS

This application is a division of U.S. patent application Ser. No. 11/119,339, filed Apr. 29, 2005, now U.S. Pat. No. 8,002,730 issued Aug. 23, 2011, and claims priority therefrom.

FIELD OF THE INVENTION

The present invention relates generally to the field of venous shunt systems and method and, more particularly, to venous shunt systems and methods used for treating hydrocephalus.

BACKGROUND OF THE INVENTION

Ventricles of the brain contain cerebrospinal fluid which cushions the brain against shock. Cerebral spinal fluid is constantly being secreted and absorbed by the body usually in equilibrium. Cerebral spinal fluid is produced in the ventricles of the brain, where under normal conditions, it is circulated in the subarachnoid space and reabsorbed into the bloodstream, predominantly via the arachnoids villi attached to the superior sagittal sinus. However, if blockages in circulation of cerebral spinal fluid, perhaps in the ventricles, cerebral spinal fluid can't be reabsorbed by the body at the proper rate.

This can create a condition known as hydrocephalus which is a condition marked by an excessive accumulation of fluid violating the cerebral ventricles, then the brain and causing a separation of the cranial bones. Hydrocephalus is a condition characterized by abnormal flow, absorption or formation of cerebrospinal fluid within the ventricles of the brain which subsequently increases the volume and pressure of the intracranial cavity. If left untreated, the increased intracranial pressure can lead to neurological damage and may result in death.

A common treatment for hydrocephalus patients has been the cerebrospinal fluid shunt. The standard shunt consists of the ventricular catheter, a valve and a distal catheter. The excess cerebrospinal fluid is typically drained from the ventricles to a suitable cavity, most often the peritoneum or the atrium. The catheter is placed into ventricles to shunt cerebral spinal fluid to other areas of the body, principally the peritoneum or alternatively to the sagittal sinus, where it can be reabsorbed. The presence of the shunt relieves pressure from cerebral spinal fluid on the brain.

A problem with venous shunt systems and methods is the possible complication of thrombus formation. A thrombus may form, for example, in the lumen of the shunting catheter or on the surface of the catheter. The same is true for a fluid flow device, e.g., a pressure or flow regulator, which may be included in the venous shunt system. Further, thrombus formation may occur near the area of the outlet tip the catheter, the so-called tip zone.

Formation of thrombus in or near the venous shunt system, whether in or on a component of the venous shunt system, could lead to blockage of flow and compromise the performance of the shunt system.

BRIEF SUMMARY OF THE INVENTION

Clogging or occluding of a venous shunt system may be prevented or corrected through the use of an anti-thrombogenic and/or clot busting agent or agents. The use of such agent or agents can be effective in preventing the formation of a thrombus or in the elimination of a thrombus already formed.

In a preferred embodiment, the present invention provides a venous shunt system adapted to shunt cerebral spinal fluid in a patient. A catheter, having a lumen, is adapted to be placed allowing cerebral spinal fluid to flow through the lumen. At least a portion of the catheter being subjected to an anti-thrombogenic treatment.

In another embodiment, the present invention provides a venous shunt system adapted to shunt cerebral spinal fluid in a patient. A fluid control device having a fluid passage is adapted to be placed allowing cerebral spinal fluid to flow through the fluid passage. A catheter having a lumen, the catheter being in fluid communication with the fluid control device. At least a portion of at least one of the catheter and the fluid control device being subjected to an anti-thrombogenic treatment.

In a preferred embodiment, the anti-thrombogenic treatment comprises an anti-thrombogenic agent delivered to a proximate area of at least one of the catheter and the fluid control device.

In a preferred embodiment, a bioresorbable matrix holds the anti-thrombogenic agent.

In a preferred embodiment, the anti-thrombogenic agent is impregnated into at least a portion of at least one of the catheter and the fluid control device.

In a preferred embodiment, at least one of the catheter and the fluid control device has a chamber for holding the anti-thrombogenic agent.

In a preferred embodiment, at least one of the catheter and the fluid control device has an anti-thrombogenic treatment surface modification.

In a preferred embodiment, at least a portion of at least one of the catheter and the fluid control device are treated with a hydrophilic agent.

In a preferred embodiment, the hydrophilic agent comprises hydrogel.

In a preferred embodiment, the hydrogel is covalently bonded to at least a portion of at least one of the catheter and the fluid control device.

In a preferred embodiment, the hydrogel is covalently bonded to at least a portion of at least one the catheter and the fluid control device using ultraviolet light.

In another embodiment, the present invention provides a method of shunting cerebral spinal fluid in a patient. A catheter is placed to allow cerebral spinal fluid to flow through the lumen. At least a portion of the catheter is subjected to an anti-thrombogenic treatment.

In another embodiment, the present invention provides a method of shunting cerebral spinal fluid in a patient. A fluid control device is placed to allow cerebral spinal fluid to flow through the fluid passage. A catheter is placed with a lumen in fluid communication with the fluid passage to allow cerebral spinal fluid to flow through the lumen. At least a portion of at least one of the flow control device and the catheter is subjected to an anti-thrombogenic treatment.

In a preferred embodiment, the subjecting step delivers an anti-thrombogenic agent to at least a portion of at least one of the flow control device and the catheter.

In a preferred embodiment, the delivering step holds the anti-thrombogenic agent in a bioresorbable matrix.

In a preferred embodiment, the delivering step impregnates at least a portion of at least one of the flow control device and the catheter with the anti-thrombogenic agent.

In a preferred embodiment, the subjecting step holds the anti-thrombogenic agent in a chamber separate from the lumen of the catheter.

In a preferred embodiment, the subjecting step provides at least a portion of at least one of the flow control device and the catheter with an anti-thrombogenic treatment surface modification.

In a preferred embodiment, the providing step treats at least a portion of at least one of the flow control device and the catheter with a hydrophilic agent.

In a preferred embodiment, the hydrophilic agent is a hydrogel.

In a preferred embodiment, the treating step covalently bonds the hydrogel to at least a portion of at least one of the flow control device and the catheter.

In a preferred embodiment, the treating step is accomplished with ultraviolet light.

In a preferred embodiment, the subjecting step injects an anti-thrombogenic agent to a proximate area of at least one of the flow control device and the catheter.

DETAILED DESCRIPTION OF THE INVENTION

The entire content of U.S. application Ser. No. 11/119,339, filed Apr. 29, 2005, is hereby incorporated by reference.

Consistent and reliable drainage of cerebral spinal fluid from one area of the body to another, e.g., from a ventricle or ventricles of the brain to another region of the body such as the peritoneum pr sagittal sinus, can be desirable. A consistent and reliable drainage method and system can minimize the expense as well as trauma and inconvenience to the patient associated with cerebral spinal fluid revision surgery and can also lesson risk to the patient due to an inoperative cerebral spinal fluid drainage system.

Figure 1:
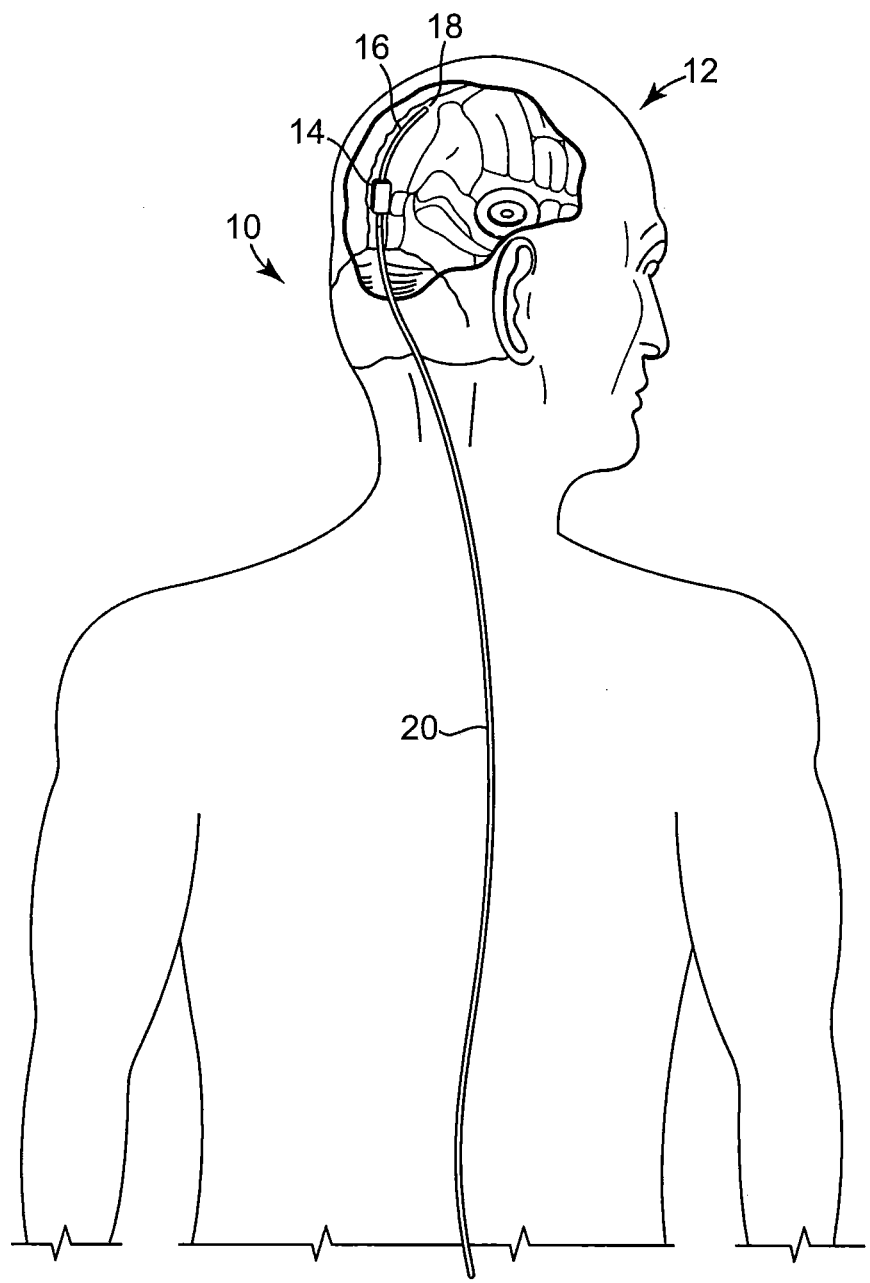
FIG. 1 is a cut-away perspective view of cerebral spinal fluid flow control device implanted into the cranium of a patient.

FIG. 1 illustrates an embodiment of a cerebral spinal fluid shunt, or drainage, system 10 for draining cerebral spinal fluid from one area, preferably the ventricles of brain, of the body of patient 12 to another area of the body of patient 12. Cerebral spinal fluid can preferably be drained to the peritoneum and/or atrium and, alternatively, to the sagittal sinus. Shunt system 10 may consist solely of a catheter having a lumen to transport cerebral spinal fluid or may consist, as illustrated in FIG. 1, flow control device 14.

Flow control device 14 may be located anywhere along the path of cerebral spinal fluid flow. For example, flow control device 14 may be located at or near the inlet for cerebral spinal fluid, e.g., at or near the ventricles, or may be located at or near the outlet for the cerebral spinal fluid, e.g., at or near the peritoneum. Alternatively, flow control device 14 may be located as illustrated in FIG. 1 along the flow path between the inlet and outlet. In particular, by way of example, flow control device 14 may be near the cranium 24.

Ventricular catheter 16, having a lumen, is connects flow control device 14 to inlet location 18 in the ventricle of patient 12. It is to be recognized and understood that other locations, other than inlet location 18, can be used. Distal catheter 20 connects flow control device 14 with an outlet for cerebral spinal fluid, not shown, which preferably is in the peritoneum. It is to be recognized and understood that other outlet locations can be used. Examples of other possible outlet locations include the atrium and the sagittal sinus.

Although not required, flow control device 14 can help alleviate cerebral spinal fluid flow differential due to different positioning of the body. For example, when the body is supine, the difference in elevation between the inlet of ventricular catheter 16 and the outlet of distal catheter 20 may be relatively small. Thus, the pressure differential due to elevation between the inlet and outlet may also be relatively small. This may result in a relatively small flow rate of cerebral spinal fluid through shunt system 10.

However, when the body is erect, for example, the difference in elevation between the inlet of ventricular catheter 16 and the outlet of distal catheter 20 may be relatively large. Thus, the pressure differential due to elevation between the inlet and outlet may also be relatively large. This may result in a relatively large flow rate of cerebral spinal fluid through shunt system 10.

The presence of a flow control device 14 in shunt system 10 can help to stabilize the rate of flow of cerebral spinal fluid through shunt system 10 by limiting the higher flow rates associated with, for example, an erect position of the body. However, it is to be recognized and understood that the present invention has applicability regardless of whether or not a flow control device is actually desired and/or utilized. However, since it is envisioned that a flow control device is generally desirable in most circumstances, the discussion hereinafter will be mostly based upon the inclusion of a flow control device. The use or inclusion of a flow control device, however, is not required.

Clogging or occluding of venous shunt system 10 may be prevented or corrected through the use of one or more anti-thrombogenic and/or clot busting agent or agents. The use of such agent or agents can be effective in preventing the formation of a thrombus or in the elimination of a thrombus already formed.

The use of the term anti-thrombogenic agent refers to an agent that is effective in preventing the coagulation or clotting of cerebral spinal fluid or other fluids in or near shunt system 10. An example of an anti-thrombogenic agent is heparin. The use of the term clot busting agent refers to an agent that is effective in clearing already existing clots or obstructions of cerebral spinal fluid or other fluids in or near shunt system 10. An example of a clot busting agent is Streptokinase or Urokinase. Although it is recognized that an anti-thrombogenic agent may be different from a clot busting agent, throughout this specification, including the claims, the use of the terms anti-thrombogenic agent, clot busting agent, either or both, is considered to refer to either agents or both agents. For the purposes of this invention, the terms are considered interchangeable since their purpose is to prevent or clear clots and/or obstructions from the path of flow of cerebral spinal fluid in shunt system 10.

Figure 2:
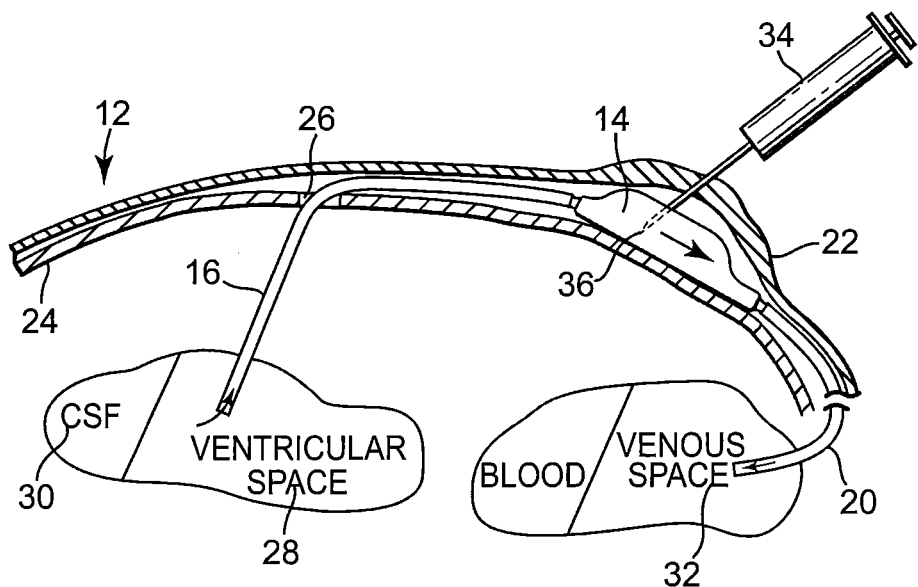
FIG. 2 is a cross-sectional side view of a venous shunt system having an anti-thrombogenic agent administered to the system.

FIG. 2 illustrates a cross-sectional view of an embodiment of the invention in which an anti-thrombogenic and/or clot busting agent is delivered, or in a preferred embodiment, injected into flow control device 14. In this schematic embodiment, not drawn to scale, flow control device 14 is implanted underneath scalp 22 exterior of cranium 24. Ventricular catheter 16 is tunneled between flow control device 14 underneath scalp 22, through burr hole 26 into ventricular space 28 containing cerebral spinal fluid 30. Distal catheter 20 is also tunneled subcutaneously between flow control device 14 and venous space 32 providing an outlet for cerebral spinal fluid from ventricular space 28.

Hypodermic needle 34 containing an anti-thrombogenic and/or clot busting agent is transcutaneously inserted with tip 36 positioned at a location where the injection of an anti-thrombogenic and/or clot busting agent would be effective in preventing or clearing an obstruction in cerebral spinal fluid shunt system 10. In a preferred embodiment illustrated in FIG. 2, tip 36 of hypodermic needle 34 is positioned within the body of flow control device 14 in order to deliver an anti-thrombogenic and/or clot busting agent to flow control device 14. The presence of an anti-thrombogenic and/or clot busting agent in flow control device 14 can help avoid or clear obstructions that might otherwise jeopardize the effectiveness and/or reliability of shunt system 10.

Alternatively, hypodermic needle 34 may be used to deliver an anti-thrombogenic and/or clot busting agent to other areas in or along the path of cerebral spinal fluid flow in or near shunt system 10. As examples, an anti-thrombogenic and/or clot busting agent may be delivered by hypodermic needle 34 to a lumen in either of ventricular catheter 16 or distal catheter 20 or both. In another alternative embodiment, an anti-thrombogenic and/or clot busting agent may be delivered by hypodermic needle 34 to an area of ventricular space 28 near the inlet of ventricular catheter 16 or may be delivered by hypodermic needle 34 to an area near the outlet of distal catheter 20 in venous space 32.

It is to be recognized and understood that other delivery mechanisms and methods, beyond the use of a hypodermic needle as illustrated in FIG. 2, are contemplated as well.

Figure 3:
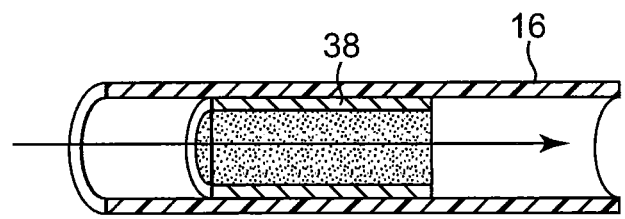
FIG. 3 is a cut-away side view of a catheter useful in a venous shunt system having an anti-thrombogenic agent associated with a bioresorbable matrix.

FIG. 3 illustrates an alternative delivery mechanism and delivery method for the delivery of an anti-thrombogenic and/or clot busting agent to shunt system 10. Bioresorbable matrix 38 is secured in the fluid flow path of shunt system 10, for example prior to implantation. Bioresorbable matrix 38 is impregnated with an anti-thrombogenic and/or clot busting agent. Anti-thrombogenic and/or clot busting agent is graduated released from bioresorbable matrix 38 while shunt system 10 is in use thus preventing or clearing clots which would otherwise obstruct the flow of cerebral spinal fluid through shunt system 10.

Bioresorbable matrix 38 is degraded biologically and may be constructed from a bioresorbable material such as the polylactic acid and lactic acid copolymers currently used in the MacroPore™ CMF™ products marketed by Medtronic, Inc., Minneapolis, Minn. In an embodiment, bioresorbable matrix 38 may be using a copolymer described in U.S. Pat. No. 4,916,193, Tang et al, Medical Devices Fabricated Totally Or In Part From Copolymers of Recurring Units Derived From Cyclic Carbonates and Lactides, the content of which is hereby incorporated be reference.

As illustrated in FIG. 3, bioresorbable matrix 38 is positioned within a lumen of ventricular catheter 16. Bioresorbable matrix 38 may also to positioned a lumen of distal catheter 20 or, alternatively, may be positioned within flow control device 14 and illustrated by flow control device 14A in FIG. 4.

Figure 4:
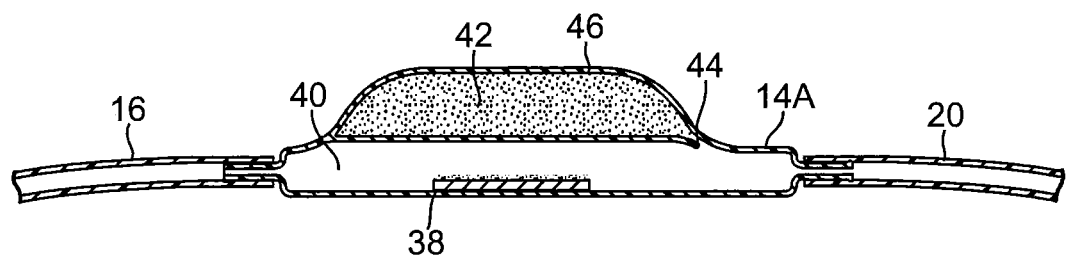
FIG. 4 is a cross-sectional side view of a device insertable into a venous shunt system having a dome containing an anti-thrombogenic agent.

FIG. 4 also illustrates an alternative delivery mechanism and method for an anti-thrombogenic and/or clot busting agent. Flow control device 14A is similar to flow control device 14 having a flow chamber 40 with an inlet fluidly coupled to ventricular catheter 16 and an outlet fluidly coupled to distal catheter 20. Also included in flow control device 14A is a conventional fluid flow control mechanism which is not explicitly shown. Such flow control mechanisms, such as a tortuous path, however, are well know in the art.

A preferred fluid control mechanism is illustrated in co-pending U.S. patent application Ser. No. 11/118,766 filed on Apr. 29, 2005 in the names of William J. Bertrand and Bill Sugleris and entitled "Implantable Cerebral Spinal Fluid Flow Device and Method of Controlling Flow of Cerebral Spinal Fluid", the contents of which are hereby incorporated by reference.

Flow control device 14A differs from flow control device 14 by having a second chamber 42 that holds a supply of anti-thrombogenic and/or clot busting agent. Second chamber 42 has an opening 44 permitting communication of anti-thrombogenic and/or clot busting agent from second chamber 42 into the fluid flow path of shunt system 10, such as into flow chamber 40 of flow control device 14A.

In a preferred embodiment, upper dome 46 may be flexible. Since flow control device 14A may be implanted subcutaneously just under scalp 22, pressure applied to scalp 22 can deform upper dome 46 forcing an amount of anti-thrombogenic and/or clot busting agent to flow from second chamber 42 through opening 44 into flow chamber 40 where the agent or agents can operate effectively to prevent or clear clots and obstructions.

While shown as part of flow control device 14A, it is to be recognized and understood that second chamber 42 could also be part of a device separate from a device that provides flow control. That is, the flow control function of flow control device 14A could be separate from the anti-thrombogenic and/or clot busting function of second chamber 42. Flow control device 14A could perform only an anti-thrombogenic and/or clot busting agent function and not a flow control function. Flow control could then, optionally, be provided in a separate device along the flow path of shunt system 10, if desired.

Figure 5:
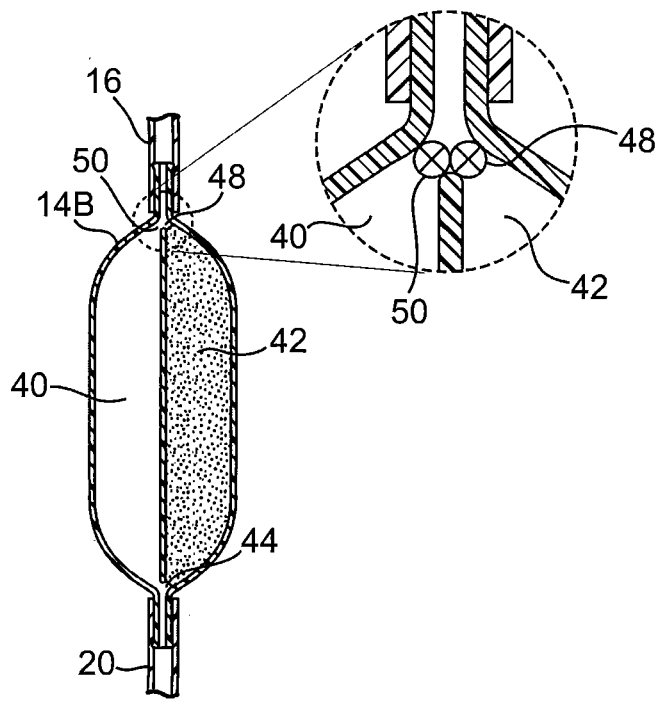
FIG. 5 is a cross-sectional side view of a device insertable into a venous shunt system having a separate, valve-controlled reservoir containing an anti-thrombogenic agent along-side a clear flow chamber.

FIG. 5 is a cross-sectional view of another embodiment of the present invention. Flow control device 14B is similar to flow control device 14A by having flow chamber 40 providing a main fluid path for cerebral spinal fluid and second chamber 42 for holding an anti-thrombogenic and/or clot busting agent. Preferably, anti-thrombogenic and/or clot busting agent is held in chamber 42 with a bioresorbable matrix as described above with respect to FIG. 3. As with flow control device 14A, opening 44 provides a path for communication of anti-thrombogenic and/or clot busting agents from second chamber 42 to the main fluid flow path of shunt system 10.

Flow control device 14B also has an opening or a one-way valve 48 positioned between a main fluid flow path of shunt system 10, in this case either flow chamber 40 or ventricular catheter 16, that will allow some of the flow of cerebral spinal fluid from ventricular catheter 16 to second chamber 42 forcing some of the anti-thrombogenic and/or clot busting agents from second chamber 42 through opening 44 into the main fluid flow path of shunt system 10. Thus, a continuing supply of anti-thrombogenic and/or clot busting agent is available to shunt system 10 relying only on the flow of cerebral spinal fluid to dispense the anti-thrombogenic and/or clot busting agents.

Optionally a low-pressure opening valve 50 may be positioned in the flow path of flow chamber 40. One-way valve 48 in this embodiment would have a higher, perhaps only slightly higher, opening pressure. Under normal, i.e., unobstructed, flow conditions, most or nearly all of the flow of cerebral spinal fluid would pass through flow chamber 40 with little or none of the flow of cerebral spinal fluid passing through second chamber 42.

Upon buildup of back pressure due to downstream clotting or obstruction of cerebral spinal fluid flow in shunt system 10, one-way valve 48 will either open or open further resulting in a flow or increased flow of cerebral spinal fluid through second chamber 42 allowing the release, or release of greater amounts of, anti-thrombogenic and/or clot busting agents.

As with flow control device 14A of FIG. 4, it is to be recognized and understood that second chamber 42 could also be part of a device separate from a device that provides flow control. That is, the flow control function of flow control device 14B could be separate from the anti-thrombogenic and/or clot busting function of second chamber 42. Flow control device 14B could perform only an anti-thrombogenic and/or clot busting agent function and not a flow control function. Flow control could then, optionally, be provided in a separate device along the flow path of shunt system 10, if desired.

As can be seen, the anti-thrombogenic and/or clot busting agent may be delivered to shunt system 10 in a number of different manners. The anti-thrombogenic and/or clot busting agent may be injected, for example as described above with respect to FIG. 2. The anti-thrombogenic and/or clot busting agent may be held in a bioresorbable matrix, for example as described above with respect to FIG. 3. The anti-thrombogenic and/or clot busting agent may be held in a second chamber, for example as described with respect to FIG. 4 and FIG. 5.

An anti-thrombogenic and/or clot busting agent may also be provided through a surface treatment modification of one or more surfaces of any or all of the components of shunt system 10. In particular, one or more of the surfaces of shunt system may be made hydrophilic through the use of well known techniques and processes. In a preferred embodiment of the present invention, one or more surfaces of shunt system 10 is made hydrophilic through the use of hydrogel. It is preferred that the hydrogel be covalently bonded to surface of an element or elements of shunt system 10 and still more preferably that such covalent bonding be accomplished with ultraviolet light. Other bonding methods may also be employed.

Suitable hydrogels include those that are 70 to 80 percent water content by weight. In a preferred embodiment, polyvinylpyrrolidone (PVP or Povidone) is utilized. PVP is ionically neutral. In other embodiments, PEG/PEO (polyethylene glycol/polyethylene oxide), PAA (polyacrylamide) and/or PVA (polyvinyl alcohol) hydrogels may be used. Other hydrogels may also be employed.

Preferably, hydrogel is surface grafted using covalent bonding to the implant surface. Coatings are held in place with Van der Waals forces, hydrogen bonding, ionic bonding or mechanical attachment. Preferably, covalent attachment, which is much stronger, is used and may be accomplished using ultraviolet light or other methods.

This treatment is similar to ultraviolet linked polyvinylpyrrolidone utilized under the tradename "BioGlide" by Medtronic, Inc., Minneapolis, Minn., for a surface modification of silicone elastomer shunts for the reduction of bacterial adhesion. This technology is described in U.S. Pat. No. 4,722,906, Guire et al, Binding Reagents and Methods; U.S. Pat. No. 4,973,493, Guire et al, Method of Improving the Biocompatibility of Solid Surfaces; U.S. Pat. No. 4,979,959, Guire et al, Biocompatible Coating For Solid Surfaces; U.S. Pat. No. 5,002,582, Guire et al, Preparation of Polymeric Surfaces Via Covalently Attaching Polymers; U.S. Pat. No. 5,217,492, Guire et al, Biomolecule Attachment To Hydrophobic Surfaces; U.S. Pat. No. 5,258,041, Guire et al, Method of Biomolecule Attachment To Hydrophobic Surfaces; U.S. Pat. No. 5,263,992, Guire et al, Biocompatible Device With Covalently Bonded Biocompatible Agent; U.S. Pat. No. 5,512,329, Guire et al, Surface Treatment Preparation, and U.S. Pat. No. 5,741,551, Guire et al, Preparation of Polymeric Surfaces, the contents of all of which are hereby incorporated by reference.

Thus, embodiments of the anti-thrombogenic venous shunt system and method are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method of shunting cerebral spinal fluid in a patient, comprising the steps of:
   placing a first fluid flow lumen of a catheter to allow cerebral spinal fluid to flow therethrough developing a fluid flow lumen pressure;
   coupling a first lumen, having a first lumen pressure, of said catheter to a second fluid flow lumen;
   coupling a second lumen having a second lumen pressure and which is deformable, defined, at least in part, by a second lumen wall, to said first lumen;
   coupling a low-pressure valve between said first fluid flow lumen and said first lumen, said cerebral spinal fluid flowing through said low-pressure valve when a difference between said fluid flow lumen pressure and said first lumen pressure is greater than a pressure rating of said low-pressure valve;
   coupling a one-way valve between said first fluid flow lumen and said second lumen, said one-way valve having a higher pressure rating than said low-pressure valve and allowing at least some cerebral spinal fluid to enter said second lumen when said difference between said fluid flow lumen pressure and said second lumen pressure is greater than said pressure rating of said one-way valve; and
   delivering an anti-thrombogenic agent into said second lumen;
   wherein said anti-thrombogenic agent is delivered to said first lumen when an external force is exerted on said second lumen wall.

2. A method as in claim 1 wherein said subjecting step comprises delivering an anti-thrombogenic agent to a proximate area of said catheter.

3. A method of shunting cerebral spinal fluid in a patient, comprising the steps of:
   placing a flow control device having a fluid passage to allow cerebral spinal fluid to flow through said fluid passage;
   placing a first fluid flow lumen of a catheter in fluid communication with said fluid passage to allow cerebral spinal fluid to flow therethrough developing a fluid flow lumen;
   coupling a first lumen, having a first lumen pressure, of said catheter to a second fluid flow lumen;
   coupling a second lumen having a second lumen pressure and which is deformable, defined, at least in part, by a second lumen wall, of said flow control device to said first lumen;
   coupling a low-pressure valve between said first fluid flow lumen and said first lumen, said cerebral spinal fluid flowing through said low-pressure valve when a difference between said fluid flow lumen pressure and said first lumen pressure is greater than a pressure rating of said low-pressure valve;

coupling a one-way valve between said first fluid flow lumen and said second lumen, said one-way valve having a higher pressure rating than said low-pressure valve and allowing at least some cerebral spinal fluid to enter said second lumen when said difference between said fluid flow lumen pressure and said second lumen pressure is greater than said pressure rating of said one-way valve; and delivering an anti-thrombogenic agent into said second lumen;

wherein said anti-thrombogenic agent is delivered to said first lumen when an external force is exerted on said second lumen wall.

4. A method as in claim 3 wherein said subjecting step comprises delivering an anti-thrombogenic agent to at least a portion of at least one of said flow control device and said catheter.

\* \* \* \* \*